US012502315B2

(12) United States Patent
McClellan et al.

(10) Patent No.: US 12,502,315 B2
(45) Date of Patent: Dec. 23, 2025

(54) PROTECTIVE EYE SHIELD

(71) Applicant: Intermed Labs @ Mon Health, LLC, Morgantown, WV (US)

(72) Inventors: William T. McClellan, Morgantown, WV (US); Ryan Gross, Morgantown, WV (US); Gavin Acquaviva, Newark, DE (US); Justin R. Chambers, Morgantown, WV (US); Ephraim Pittore-Candelario, Morgantown, WV (US)

(73) Assignee: INTERMED LABS @ MON HEALTH, LLC, Morgantown, WV (US)

( * ) Notice: Subject to any disclaimer, the term of this patent is extended or adjusted under 35 U.S.C. 154(b) by 470 days.

(21) Appl. No.: 17/835,036

(22) Filed: Jun. 8, 2022

(65) Prior Publication Data

US 2022/0387221 A1 Dec. 8, 2022

Related U.S. Application Data

(60) Provisional application No. 63/208,205, filed on Jun. 8, 2021.

(51) Int. Cl.
*A61F 9/04* (2006.01)

(52) U.S. Cl.
CPC .......... *A61F 9/04* (2013.01); *A61F 2210/009* (2013.01); *A61F 2220/0008* (2013.01); *A61F 2220/0033* (2013.01); *A61F 2220/0091* (2013.01); *A61F 2250/0091* (2013.01)

(58) Field of Classification Search
CPC ........ A61F 2220/0008; A61F 2210/009; A61F 13/12; A61F 9/00; A61F 9/022; A61F 9/04
USPC ................................ 2/15; 128/846, 857, 858
See application file for complete search history.

(56) References Cited

U.S. PATENT DOCUMENTS

| | | | | | |
|---|---|---|---|---|---|
| 4,549,539 | A * | 10/1985 | Donaldson | A61F 9/00718 | 604/294 |
| 4,709,695 | A * | 12/1987 | Kohn | A61F 9/04 | 128/858 |
| 4,898,162 | A * | 2/1990 | Worthrich | A61F 15/004 | 2/909 |
| 5,843,025 | A * | 12/1998 | Shaari | A61F 13/00085 | 602/53 |
| 10,821,025 | B1 * | 11/2020 | Stravitz | A61F 9/04 | |
| 2005/0274387 | A1 * | 12/2005 | MacKen | A61F 5/56 | 128/848 |

(Continued)

FOREIGN PATENT DOCUMENTS

| | | | | |
|---|---|---|---|---|
| WO | WO-2015024076 A1 * | 2/2015 | A61F 13/124 |
| WO | WO-2016064731 A1 * | 4/2016 | A61F 9/025 |

*Primary Examiner* — Caitlin A Carreiro
(74) *Attorney, Agent, or Firm* — Calderon Safran & Wright P.C.

(57) ABSTRACT

A wearable medical device assembly for therapeutic treatment of a person includes: a wearable medical device configured to be applied over a portion of the person; a first anchor and a second anchor each including an adhesive configured to affix the respective anchor to the person's skin; and an attachment system that selectively attaches the wearable medical device to the first anchor and the second anchor, wherein the attachment system permits the wearable medical device to be detached from, and re-attached to, one or both of the anchors while both of the anchors remain affixed to the person's skin.

1 Claim, 10 Drawing Sheets

(56) References Cited

U.S. PATENT DOCUMENTS

2019/0046797 A1* 2/2019 Calixto ................ A61N 1/0541

* cited by examiner

PROTECTIVE EYE SHIELD

PRIORITY

This application claims priority to provisional application No. 63/208,205 filed Jun. 8, 2021, the disclosure of which is incorporated by reference herein in its entirety.

FIELD OF THE INVENTION

The invention generally relates to medical devices and associated methods of manufacture and use, and more particularly to protective eye shields.

BACKGROUND

The use of the eye shield is designed to create a barrier between the eye and the outside world to avoid any unwanted complications during the eye's healing process using what seems as though is a simple piece of plastic attached by tape. Shields are generally affixed to the patient's face in a diagonal direction from cheek to the mid-eyebrow region for a snug fit. FIG. 1 shows a prior art eye shield 100 that is affixed to the patient using strips of tape 105. Doctors may have their affixment be slightly different, however such orientations are generally agreed upon. Although the technique of using eye shields has been effective, the consensus is that while the design is simple and cheap to produce, the usage of tape to affix the shield to the eye presents a cost issue over time given tape can't be reutilized after application. Additionally, the tape presents problems to the patient such as skin sensitivity, irritation, etc. that makes it unpleasant for many patients.

SUMMARY

Implementations of the invention address the above-noted problems of the prior art by providing an eye shield that is easily detachable and re-attachable without using tape. Implementations include an eye shield with an attachment system that is configured to selectively attach and detach the eye shield to and from a semi-permanent anchor that is affixed to the patient's face. According to aspects of the invention, the anchor remains attached to the patient's face when the eye shield is detached from the anchor. In this manner, the eye shield may be temporarily detached from the patient, for example to permit examination of the eye by a doctor, and then reattached to the same anchor, all without removing the anchor from the patient's skin.

In a first aspect of the invention, there is a wearable medical device assembly for therapeutic treatment of a person, the wearable medical device assembly including: a wearable medical device configured to be applied over a portion of the person; a first anchor and a second anchor each comprising an adhesive configured to affix the respective anchor to the person's skin; and an attachment system that selectively attaches the wearable medical device to the first anchor and the second anchor, wherein the attachment system permits the wearable medical device to be detached from, and re-attached to, one or both of the anchors while both of the anchors remain affixed to the person's skin.

In embodiments, the wearable medical device comprises an eye shield that is configured to cover an eye of the person, and the first anchor and the second anchor are configured to be affixed to the person's face.

In embodiments, the attachment system includes: a first magnet in a first end of the wearable medical device; a second magnet in a second end of the wearable medical device opposite the first end; a third magnet in the first anchor; and a fourth magnet in the second anchor. In embodiments, the attachment system further includes: a first cavity at one of the first magnet and the third magnet, and a first protrusion at the other one of the first magnet and the third magnet, respectively, wherein the first protrusion is in the first cavity when the first end of the wearable medical device is attached to the first anchor; and a second cavity at one of the second magnet and the fourth magnet, and a second protrusion at the other one of the second magnet and the fourth magnet, respectively, wherein the second protrusion is in the second cavity when the second end of the wearable medical device is attached to the second anchor.

In embodiments, the wearable medical device assembly includes at least one living hinge in the wearable medical device. The at least one living hinge may include at least one of: a first living hinge between a central portion of the wearable medical device and a first location where the wearable medical device attaches to the first anchor; and a second living hinge between the central portion of the wearable medical device and a second location where the wearable medical device attaches to the second anchor.

In embodiments, the attachment system includes: a first snap attachment system between a first end of the wearable medical device and the first anchor; and a second snap attachment system between a second end of the wearable medical device and the second anchor. In an embodiment, the first anchor includes a first protrusion that comprises a male half of the first snap attachment system, the first end of the wearable medical device includes a first cavity that comprises a female half of the first snap attachment system, the second anchor includes a second protrusion that comprises a male half of the second snap attachment system, and the second end of the wearable medical device includes a second cavity that comprises a female half of the second snap attachment system. In an embodiment, the first end of the wearable medical device comprises a first hinge release mechanism configured to change a shape of the first cavity, and the second end of the wearable medical device comprises a second hinge release mechanism configured to change a shape of the second cavity. In an embodiment, the first end of the wearable medical device resiliently returns to a first default shape after release of a force applied to the first hinge release mechanism, and the second end of the wearable medical device resiliently returns to a second default shape after release of a force applied to the second hinge release mechanism.

In embodiments, there is a method of using the wearable medical device assembly, the method including: attaching the wearable medical device to the first anchor and the second anchor; affixing the first anchor and the second anchor to the patient's skin; detaching the wearable medical device from one or more of the first anchor and the second anchor while the first anchor and the second anchor remain affixed to the patient's skin; and reattaching the wearable medical device to the one or more of the first anchor and the second anchor while the first anchor and the second anchor remain affixed to the patient's skin.

In another aspect of the invention, there is a device for therapeutic treatment of a person, the device including: a wearable medical device configured to be applied over a portion of the person; wherein a first end of the wearable medical device comprises a first portion of a first attachment system that selectively attaches the first end of the wearable medical device to a first anchor that is configured to be affixed to the person's skin; wherein a second end of the wearable medical device comprises a first portion of a second attachment system that selectively attaches the second end of the wearable medical device to a second anchor that is configured to be affixed to the person's skin; and wherein the first attachment system and the second attachment system permit the wearable medical device to be detached from, and re-attached to, one or both of the anchors while both of the anchors remain affixed to the person's skin.

In embodiments, the wearable medical device comprises an eye shield that is configured to cover an eye of the person, and the first anchor and the second anchor are configured to be affixed to the person's face.

In embodiments, the first attachment system comprises: a first magnet in the first end of the wearable medical device, and a third magnet in the first anchor; and the second attachment system comprises: a second magnet in the second end of the wearable medical device, and a fourth magnet in the second anchor.

In embodiments, there is at least one living hinge in the wearable medical device.

In embodiments, the first attachment system comprises a first snap attachment system between the first end of the wearable medical device and the first anchor, and the second attachment system comprises a second snap attachment system between the second end of the wearable medical device and the second anchor. In an embodiment, the first end of the wearable medical device includes a first cavity that comprises a female half of the first snap attachment system, the first cavity be configured to receive and selectively retain a first protrusion of the first anchor; and the second end of the wearable medical device includes a second cavity that comprises a female half of the second snap attachment system, the second cavity be configured to receive and selectively retain a second protrusion of the second anchor. In an embodiment, the first end of the wearable medical device comprises a first hinge release mechanism configured to change a shape of the first cavity; and the second end of the wearable medical device comprises a second hinge release mechanism configured to change a shape of the second cavity. In an embodiment, the first end of the wearable medical device resiliently returns to a first default shape after release of a force applied to the first hinge release mechanism; and the second end of the wearable medical device resiliently returns to a second default shape after release of a force applied to the second hinge release mechanism.

In an embodiment, a method of using the device includes: attaching the wearable medical device to the first anchor and the second anchor; affixing the first anchor and the second anchor to the patient's skin; detaching the wearable medical device from one or more of the first anchor and the second anchor while the first anchor and the second anchor remain affixed to the patient's skin; and reattaching the wearable medical device to the one or more of the first anchor and the second anchor while the first anchor and the second anchor remain affixed to the patient's skin.

BRIEF DESCRIPTION OF THE SEVERAL VIEWS OF THE DRAWINGS

Aspects of the present invention are described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details in more detail than is necessary for the fundamental understanding of aspects of the present invention, the description taken with the drawings making apparent to those skilled in the art how several forms of the present invention may be embodied in practice.

Figure 1:
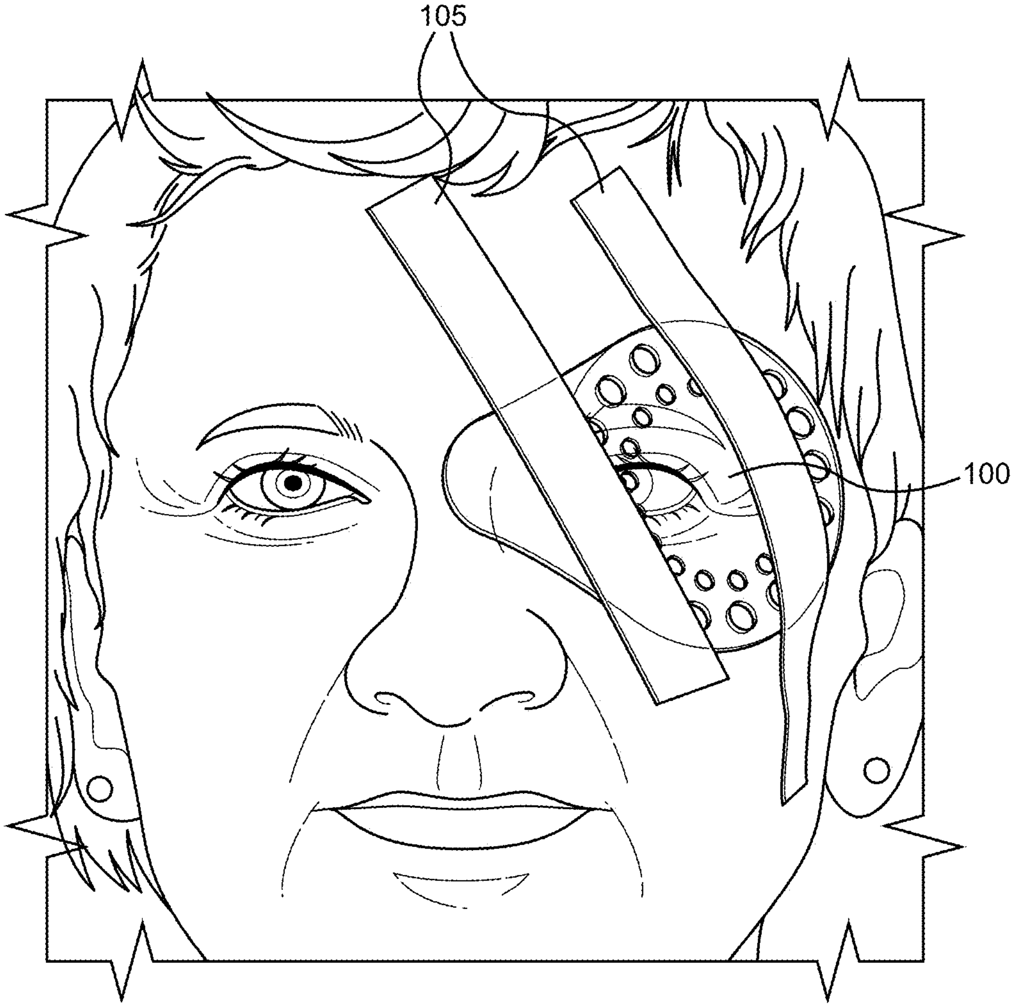
FIG. 1 Prior Art
FIG. 1 shows a prior art eye shield.
Figure 2:
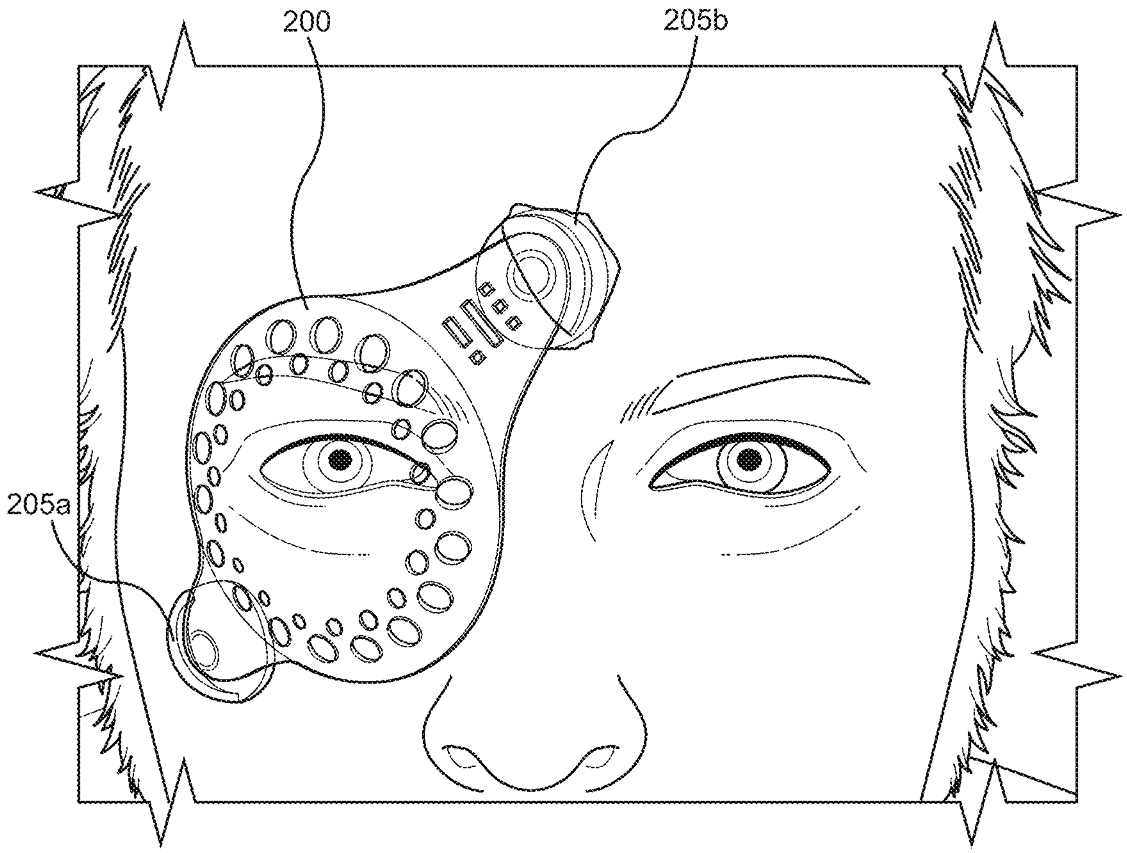
FIG. 2 shows an eye shield assembly in accordance with aspects of the invention.

FIG. 2 shows an exemplary eye shield 200 in accordance with aspects of the invention. As shown in FIG. 2, the eye shield 200 is secured over the patient's eye cavity in an orientation that is generally from cheek to the mid-brow line with the bottom of the tear-drop shape pointing in the upward direction. According to aspects of the invention, the eye shield 200 includes a first end and a second end, the first end being connected to a first anchor 205*a* affixed to the patient's face at a first location and the second end being affixed to a second anchor 205*b* affixed to the patient's face at a second location. In accordance with aspects of the invention, the eye shield 200 is selectively detachable from the anchors 205*a*, 205*b* while the anchors 205*a*, 205*b* remain affixed to the patient's face. In this manner, the eye shield 200 may be temporarily detached from one or both anchors 205*a*, 205*b*, for example to permit examination of the eye by a doctor, and then reattached to the same anchors, all without removing the anchors 205*a*, 205*b* from the patient's skin.

In embodiments, the eye shield 200 is made of polycarbonate due to its ease of manufacturability and structural properties. Other suitable materials may also be used to construct the eye shield 200. The eye shield 200 may be transparent (e.g., clear), translucent (e.g., tinted), or opaque.

Figure 3B:
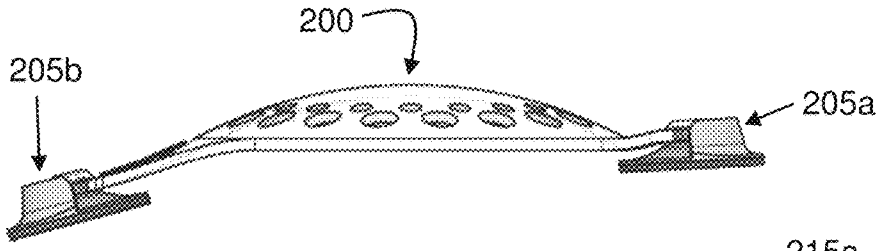
FIGS. 3A-D show an example of an eye shield assembly in accordance with aspects of the invention.
Figure 3A:
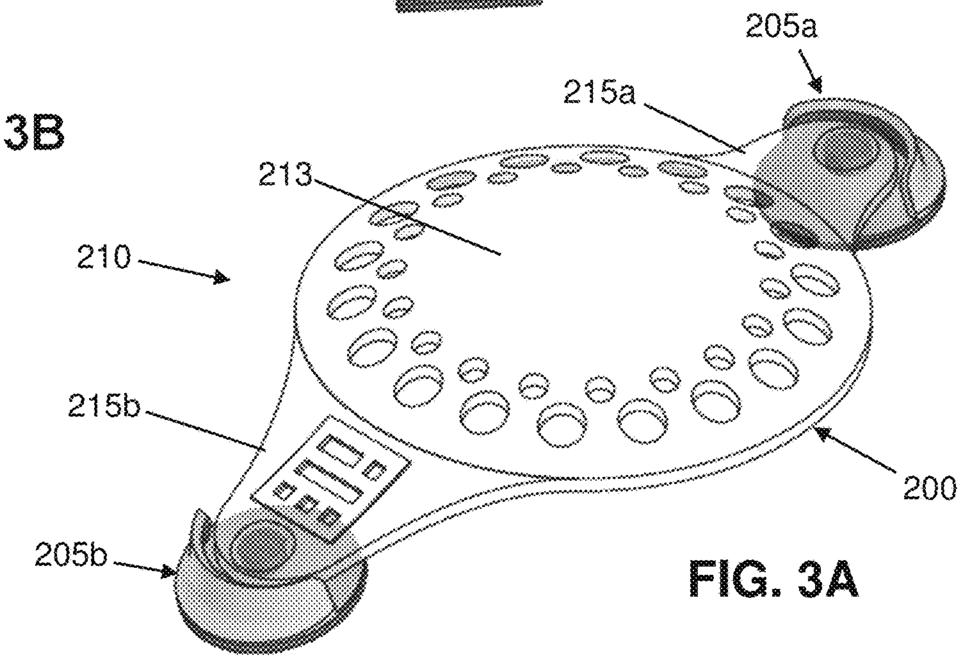
Figure 3C:
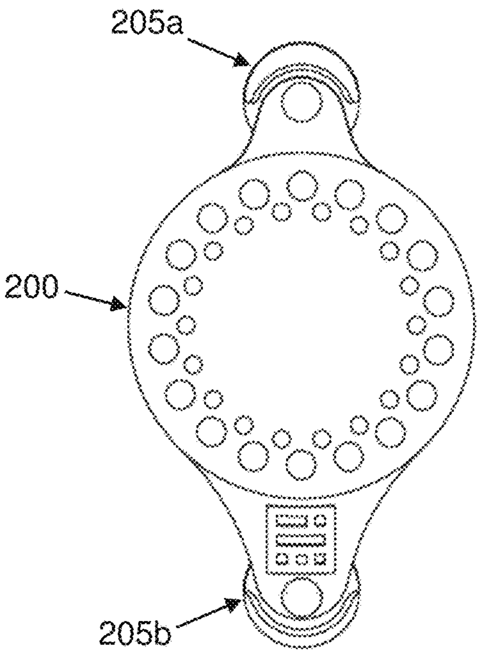
Figure 3D:
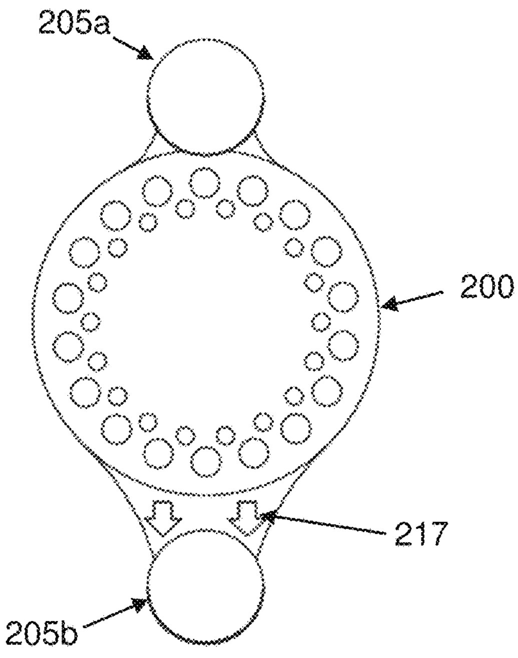

FIGS. 3A-D show an example of an eye shield assembly 210 in accordance with aspects of the invention. FIG. 3A shows an isometric view of the eye shield assembly 210, while FIGS. 3B, 3C, and 3D show a side view, top view, and bottom view, respectively, of the eye shield assembly 210.

As shown in FIGS. 3A-D, the eye shield assembly 210 includes eye shield 200 and anchors 205*a*, 205*b*. In embodiments, the eye shield 200 includes a main portion 213, a first end 215*a* extending from a first side of the main portion 213, and a second end 215*b* extending from a second side of the main portion 213 opposite the first side. In embodiments, the main portion 213 is configured to cover a patient's eye when the eye shield assembly 210 is affixed to the patient's face. The main portion 213 may have a circular shape as shown in FIGS. 3A-D or any other suitable shape. The main portion 213 may have multiple through holes that reduce the weight of the eye shield 200 and promote airflow in the area around the patient's eye. In embodiments, the first end 215*a* and the second end 215*b* are configured to selective attach the eye shield to the anchors 205*a*, 205*b*. In one example, the attachment may be made using magnets, as in the examples shown in FIGS. 3A-D. In another example, the attachment may be made using a snap connection system, as described later with respect to FIGS. 12-18.

In embodiments, in order to simplify the alignment of the system, the bottom of the eye shield 200 has one or more indicia 217 in order for the wearer to know the correct upward direction of the eye shield assembly 210, as shown in FIG. 3D. In one example, the indicia 217 comprise two arrows formed (e.g., embedded) in the material of the eye shield 200. Other types of indicia 217 may be used, and the indica 217 may be affixed to, printed on, or formed in the material of the eye shield 200.

Figure 4:
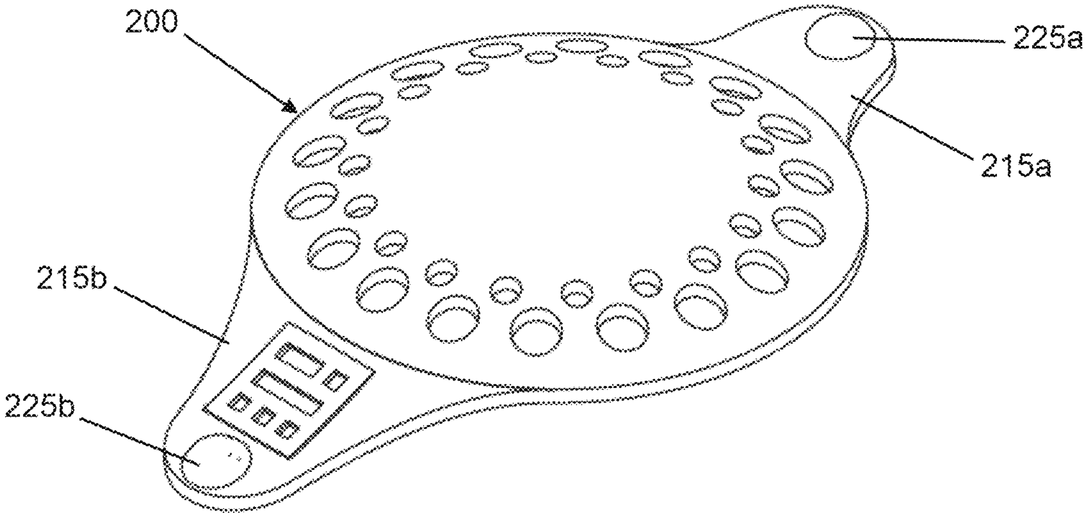
FIG. 4 shows the eye shield of FIGS. 3A-D detached from the anchors in accordance with aspects of the invention.

FIG. 4 shows the eye shield 200 of FIGS. 3A-D detached from the anchors 205*a*, 205*b*. In embodiments, and as shown in FIG. 4, the first end 215*a* comprises a first location 225*a* that contains a magnet that is configured to be attracted by magnetic force to a corresponding magnet in the first anchor 205*a*. Similarly, the second end 215*b* comprises a second location 225*b* that contains a magnet that is configured to be attracted by magnetic force to a corresponding magnet in the second anchor 205*b*.

Figure 5A:
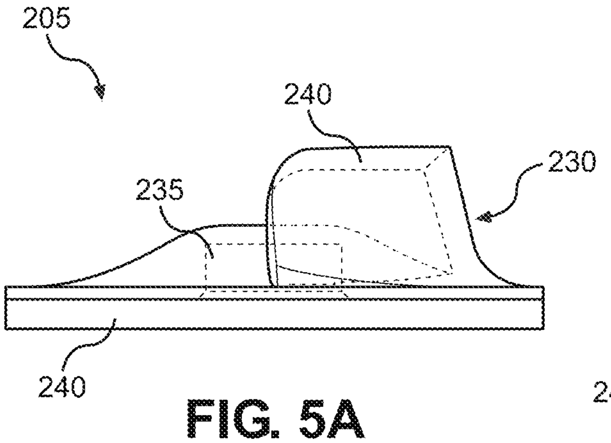
FIGS. 5A and 5B show views of an anchor in accordance with aspects of the invention.
Figure 5B:
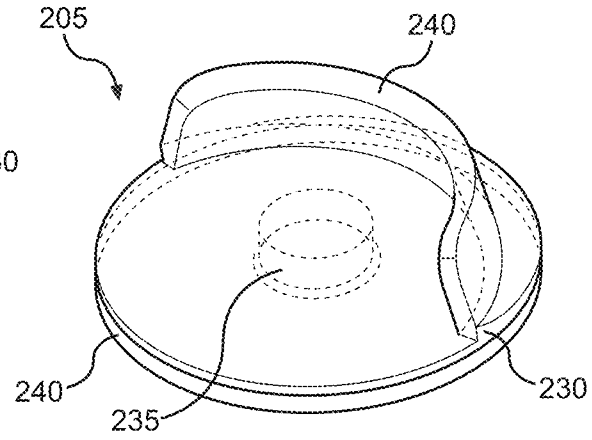

FIG. 5A shows a side view of an anchor 205 and FIG. 5B shows an isometric view of the anchor 205 in accordance with aspects of the invention. Respective instances of the anchor 205 may be used as the first anchor 205*a* and second anchor 205*b* of the eye shield assembly 210 of FIGS. 3A-D.

In embodiments, the anchor 205 includes a housing 230, a magnet 235, and a skin adhesive 240. The housing 230 may be constructed of any suitable material such as plastic, silicone, rubber, etc. In embodiments, the housing 230 includes a flange 240 on its top side, the flange 240 being configured to help retain the shield 200 onto the patient by creating a clip like feature. The flange 240 overhangs the ends 215*a* and 215*b* where by the overhang can be pulled away from the shield to help unclip the magnetic connection. As shown in FIGS. 5A and 5B, the skin adhesive 240 is on a bottom side of the housing 230 opposite the top side of the housing 230. Any suitable adhesive may be used, such as DuoDerm or similar thick dressings. In one example, the skin adhesive 240 comprises a substrate (e.g., foam) with a top of the substrate being affixed to the bottom side of the housing 230 (e.g., by welding, adhesive, etc.) and a bottom side of the substrate having an adhesive that is designed to be used with human skin. A peelable backing layer may cover the adhesive on the bottom side of the substrate until the anchor 205 is ready to be affixed to patient, at which time the health care provider may peel away the backing layer to expose the adhesive and then affix the anchor 205 to the patient's skin utilizing the now exposed adhesive.

With continued reference to FIGS. 5A and 5B, in embodiments the magnet 235 is embedded in the housing 230. As described herein, the magnet 235 is configured to be attracted by magnetic force to a corresponding magnet in the eye shield 200, thereby providing a force that attaches the eye shield 200 to the anchor 205. The magnet 235 may be a neodymimum magnet or other suitable type of magnet. In this manner, the anchor 205 provides a magnetic surface where the eye shield 200 can be affixed. Additionally, the anchor functions as an alignment point for removal and reapplication of the eye shield 200.

Figure 6:
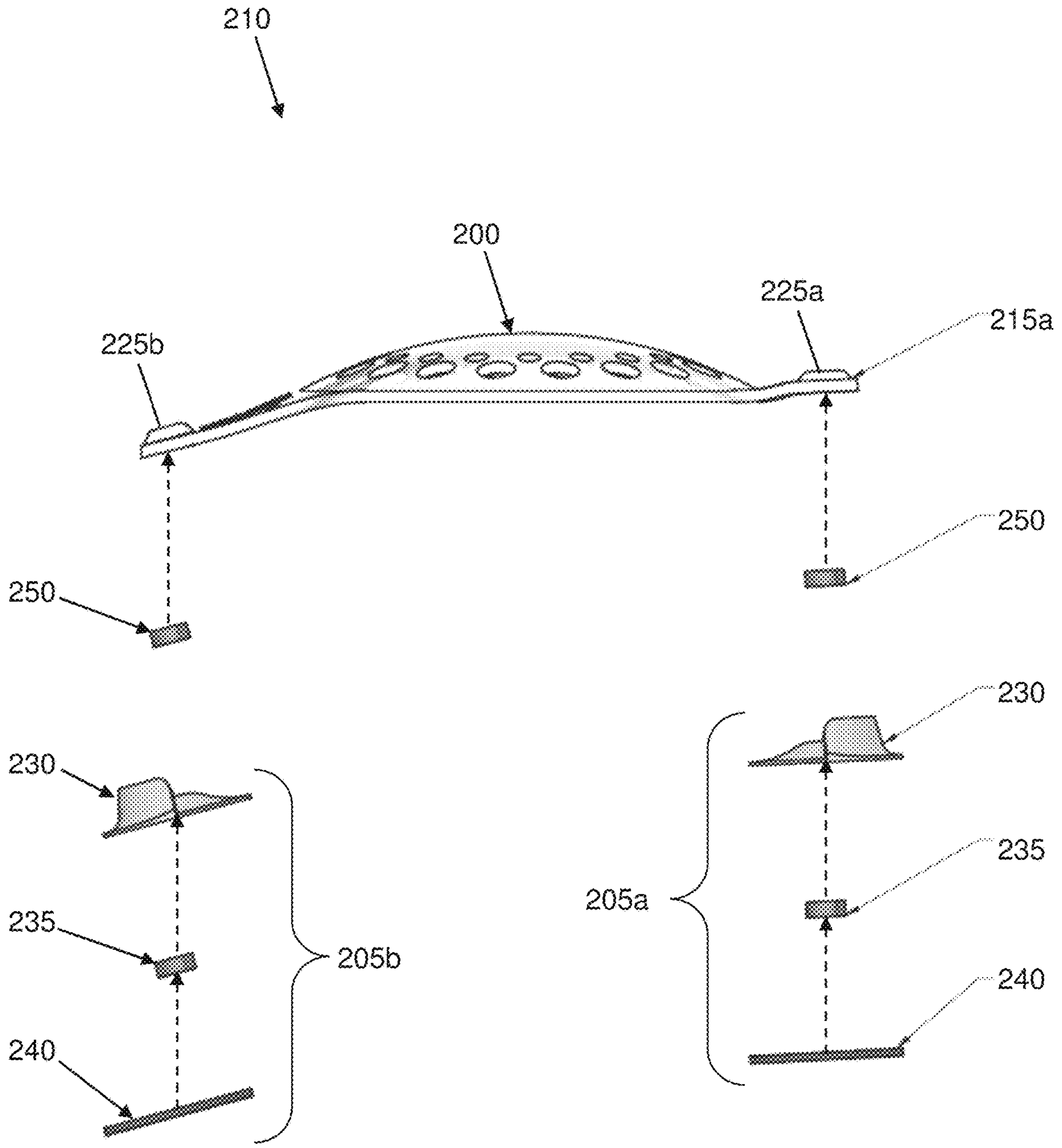
FIG. 6 shows an exploded view of the eye shield assembly of FIGS. 3A-D in accordance with aspects of the invention.

FIG. 6 shows an exploded view of the eye shield assembly 210 of FIGS. 3A-D. As shown in FIG. 6, respective magnets 250 are in the first and second locations 225*a*, 225*b* of the eye shield 200. As also shown in FIG. 6, the first anchor 205*a* and the second anchor 205*b* each comprise a housing 230, magnet 235, and skin adhesive 240. This exemplary layout consists of the use of a total of four neodymium magnets (two each of 235 and 250), two circular skin adhesives, and injection molded polycarbonate parts. While the magnets create the reusability that makes this product so special, the use of other adhesive types such as Velcro or purse clasps could also be used in their place in order to further simplify both cost and the manufacturing process.

An exemplary method of using the eye shield assembly 210 comprises: the patient removes all facial obstructions that may interfere with the application of the eye shield; opening a package including the eye shield 200 and two anchors 205*a*, 205*b*; attaching the eye shield 200 to the anchors 205*a*, 205*b* (by magnetic force a described herein) prior to affixing the anchors 205*a*, 205*b* to the patient's face; removing the peelable backing from the skin adhesive each of the anchors 205*a*, 205*b*; aligning the eye shield 200 over the patient's eye using the indicia 217 to properly orient the eye shield 200 relative to the patient's face; while the eye shield 200 is aligned over the patient's eye, pressing the anchors 205*a*, 205*b* against the patient's skin, thereby affixing the eye shield assembly 210 to the patient's face over the patient's eye, e.g., as shown in FIG. 2.

In a particular embodiment of the eye shield assembly 210, the magnets 235 and 250 and the skin adhesive 240 are selected to satisfy two conditions. The first condition is that the magnetic force between the magnets 235 and 250 is of a sufficient magnitude to hold the weight of the eye shield 200 when the eye shield is attached to the anchors 205*a*, 205*b*. The second condition is that the magnetic force between the magnets 235 and 250 is less than the adhesive force of the skin adhesive 240 on the patient's skin. By selecting the components to satisfy these conditions, the assembly is configured such that the eye shield 200 remains attached to the anchors 205*a*, 205*b* using only the magnetic force between the magnets 235 and 250 (as a result of the first condition), and the eye shield 200 can be detached from the anchors 205*a*, 205*b* without accidentally pulling the anchors 205*a*, 205*b* off the patient's skin (as a result of the second condition).

Figure 7:
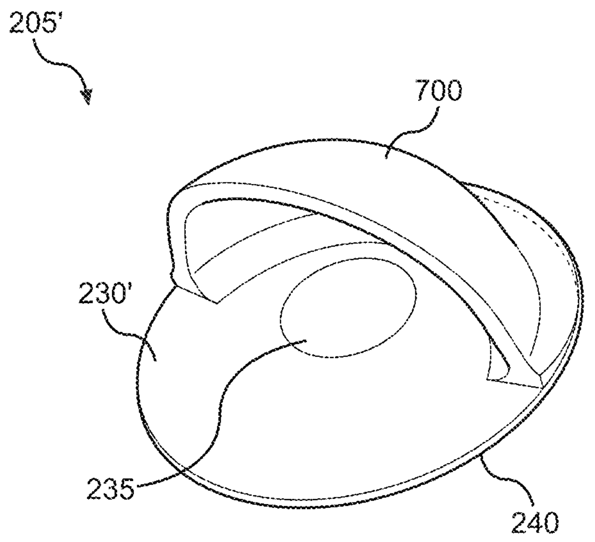
FIG. 7 shows an example of a differently shaped anchor in accordance with aspects of the invention.

FIG. 7 shows an example of a differently shaped anchor 205' in accordance with aspects of the invention. The anchor 205' includes a housing 230', magnet 235, and skin adhesive 240 similar to anchor 205. However, in this embodiment, the housing 230' includes a hood 700 that is configured to prevent shear stresses during movement and also prevent the eye shield 200 from falling off the face. In embodiments, the hood 700 has a substantially half-dome shape as shown in FIG. 7, the hood 700 being configured to cover the distal portion of the first end 215*a* or second end 215*b* of the eye shield 200. The anchor 205' including the hood 700 has been tested and proven to be an effective way to counteract the eye shield 200 being accidentally detached through normal movement of the patient wearing the eye shield assembly; however, the eye shield 200 can still be detached from the anchors easily by the patient or health care provider, when desired, by slightly spreading the patient's skin between the cheek and eyebrow region.

Figure 8:
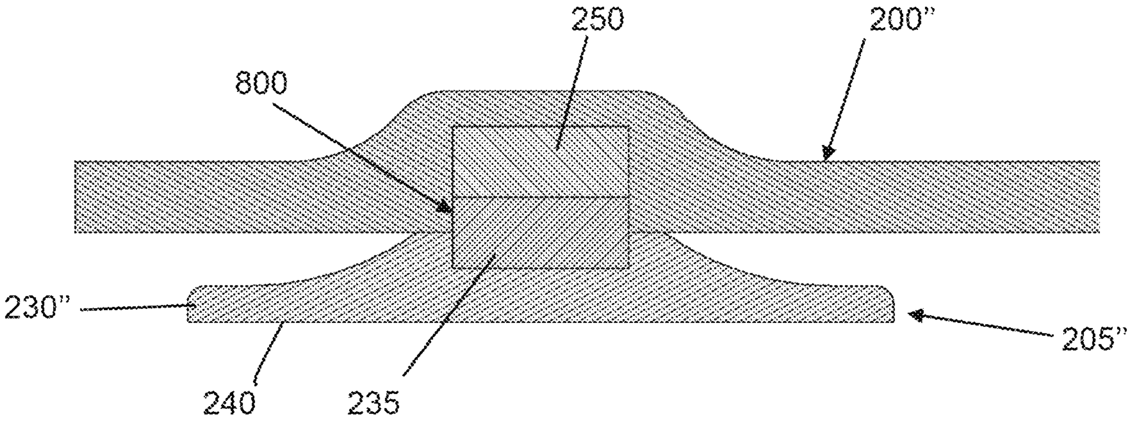
FIG. 8 shows an example of a differently shaped eye shield and anchor in accordance with aspects of the invention.

FIG. 8 shows an example of a differently shaped eye shield 200" and anchor 205" in accordance with aspects of the invention. The anchor 205" includes a housing 230", magnet 235, and skin adhesive 240 similar to anchor 205. However, in this embodiment, the magnet 235 extends outward from the uppermost surface of the housing 230" thereby creating a protrusion at the top side of the anchor 205". The eye shield 200" may be similar to eye shield 200 in that it comprises a main portion, a first end extending from a first side of the main portion, and a second end extending from a second side of the main portion. However, in this embodiment, the eye shield 200" includes a cavity 800 underneath and aligned with each magnet 250, the cavity 800 being sized and shaped to receive the protruding upper portion of the magnet 235 of the anchor 205". In this manner, the cavity 800 and the protruding upper portion of the magnet 235 together create an alignment key for positioning the eye shield 200" relative to the anchor 205". This design eliminates the need to focus on shear forces as this design would compensate for that occurrence but also be fairly simple to assemble. Alternatively, the cavity may be formed on the anchor and the protrusion may be formed on the eye shield.

Figure 9:
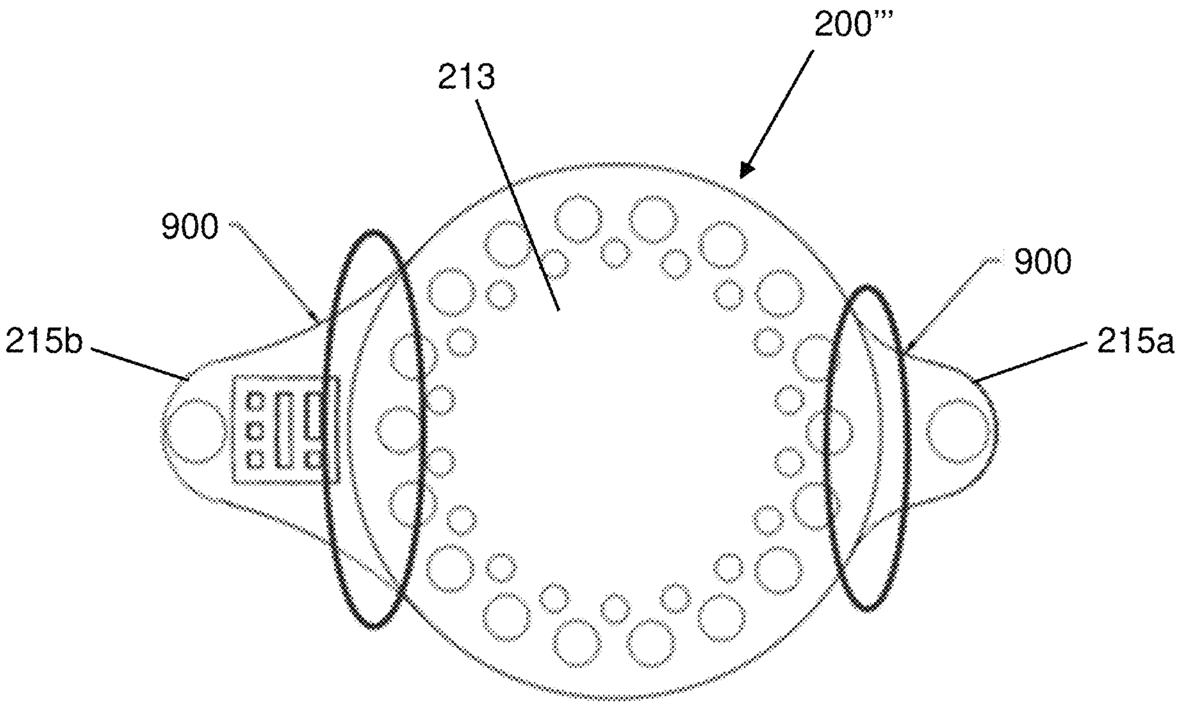
FIGS. 9 and 10 show an example of a differently shaped eye shield in accordance with aspects of the invention.
Figure 10:
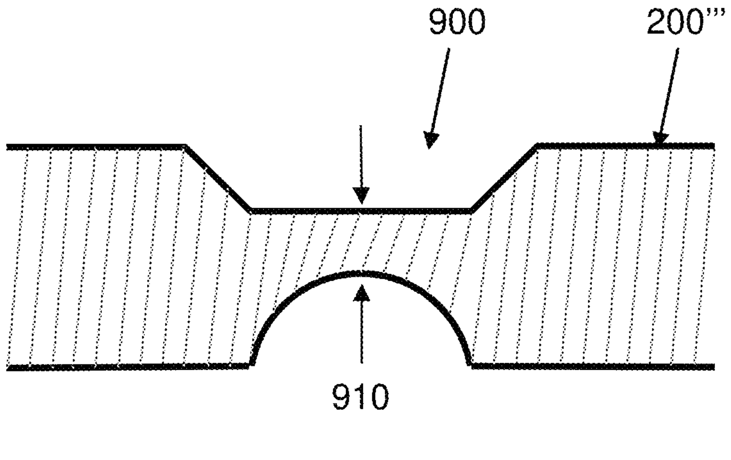

FIGS. 9 and 10 show an example of a differently shaped eye shield 200'" in accordance with aspects of the invention. The eye shield 200'" may be similar to eye shield 200 in that it comprises a main portion 213, a first end **215*a* extending from a first side of the main portion 213, a second end 215*b* extending from a second side of the main portion 213, and respective magnets at the first end 215*a* and the second end 215*b* for connecting the eye shield to anchors (e.g., anchors 205, not shown). However, in this embodiment, the eye shield 200'" includes at least one living hinge 900, an example of which is shown in FIG. 10. As shown in FIG. 9, a living hinge 900 may be formed in the eye shield 200'" between the main portion 213 and the first end 215*a* and/or between the main portion 213 and the second end 215*b*. As shown in FIG. 10, the living hinge 900 is a thinned portion 910 of the eye shield 200" that allows more flexure of the eye shield 200" compared to the amount of flexure possible at other portions of the eye shield 200'" not at the living hinge 900. In embodiments, the use of the living hinge 900 is implemented in the eye shield 200'" around the regions where the eye shield 200'" is connected to the anchors, in order to create a flexible movement to gain more accurate fit to the patient. In embodiments, the living hinge 900 is created using a thin band of material of the eye shield 200'"** that allows for much greater flex than its thicker surroundings, giving the impression of a hinge movement while still being one continuous part.

Figure 11:
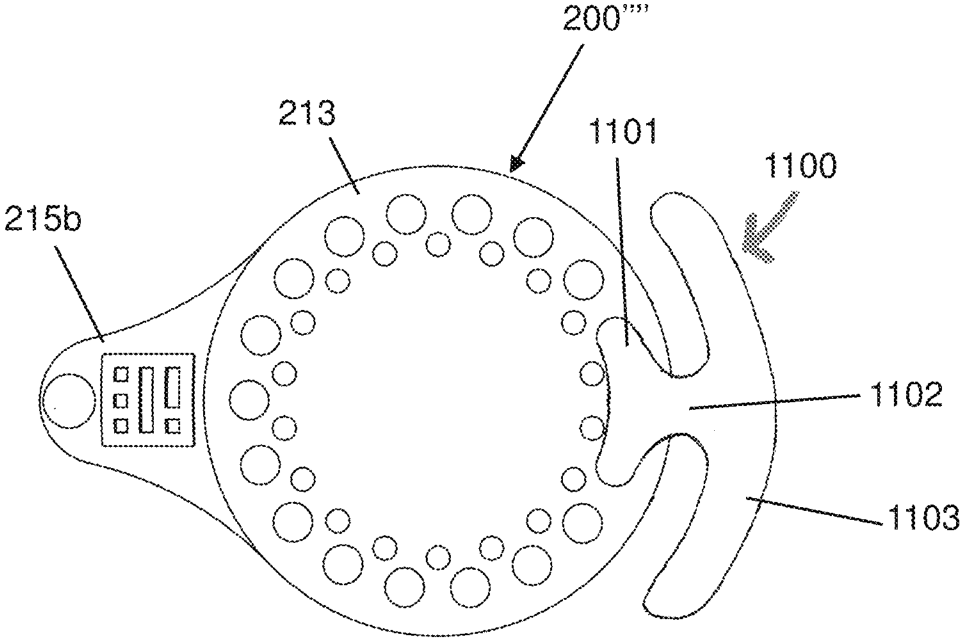
FIG. 11 shows an example of a differently shaped eye shield in accordance with aspects of the invention.

FIG. 11 shows an example of a differently shaped eye shield 200"" in accordance with aspects of the invention. The eye shield 200"" may be similar to eye shield 200 in that it comprises a main portion 213, a second end **215*b* extending from a second side of the main portion 213, and a magnet at the second end 215*b* for connecting the eye shield to an anchor (e.g., anchor 205, not shown). However, in this embodiment, the eye shield 200"" includes an adhesive fastener 1100 at the first side of the main portion 213 opposite the second end 215*b*. In embodiments, the adhesive fastener 1100 has a first portion 1101 connected to the main portion 213, a second portion 1102 configured to be attached to the face of the patient, and a third portion 1103 between the first portion 1101 and the second portion 1102. In embodiments, the second portion 1102 is significantly larger than the third portion 1103, such that the second portion 1102 has a large surface area for providing adhesion to the patient's face while the third portion 1103 acts as a living hinge that provide flexibility. In a particular embodiment, the second portion 1102 has a semicircular or curved shape. In use, the second portion 1102 remains affixed to the patient's face while the second end 215*b* is selectively attached to and detached from its corresponding anchor (e.g., anchor 205, not shown). This design allows the user to detach the second end 215*b* (via the magnet) to hinge the eye shield 200"" to perform medical procedures or maintenance using the flexible properties of the adhesive fastener 1100. Alternative fastening methods, such as Velcro, can also be used to replace the magnetic clasp features. For example, the eye shield 200"" may include a piece of Velcro at the second end 215*b* (instead of a magnet 250), and the anchor (e.g., anchor 205, not shown) may include a piece of Velcro that is configured to mate with the Velcro of the second end 215*b*. In this manner, the anchor may remain affixed to the patient's skin and the eye shield 200""** may be selectively attached to and detached from the anchor using the Velcro.

Figure 12:
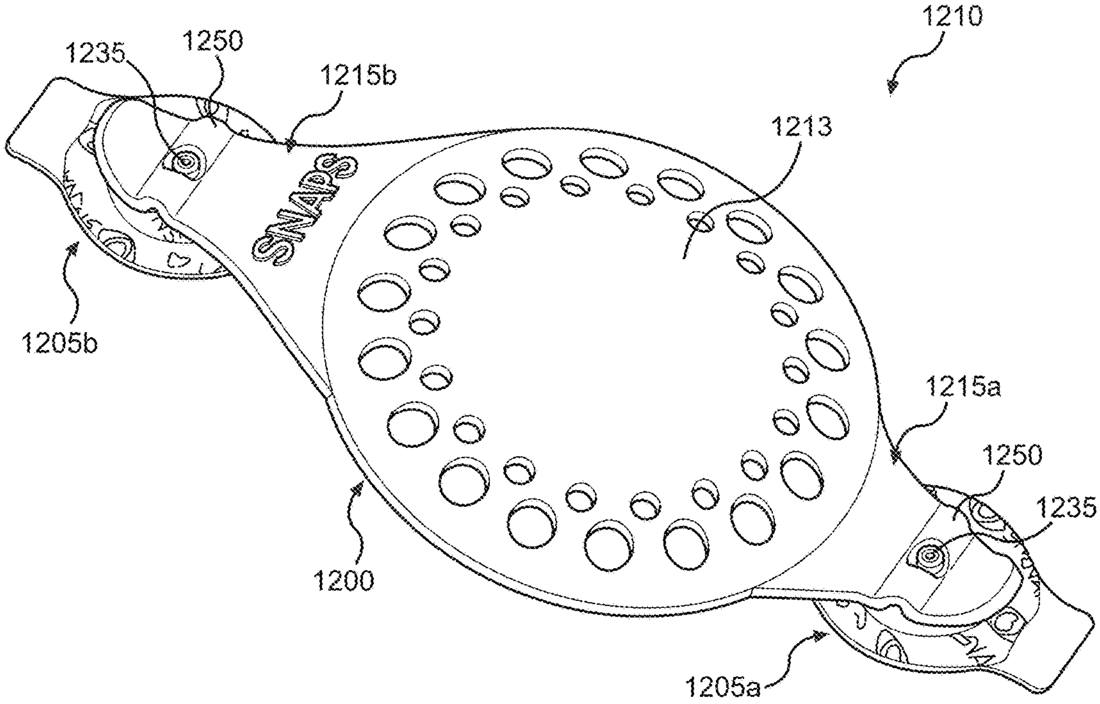
FIGS. 12-18 show an example of an eye shield assembly in accordance with aspects of the invention.
Figure 13:
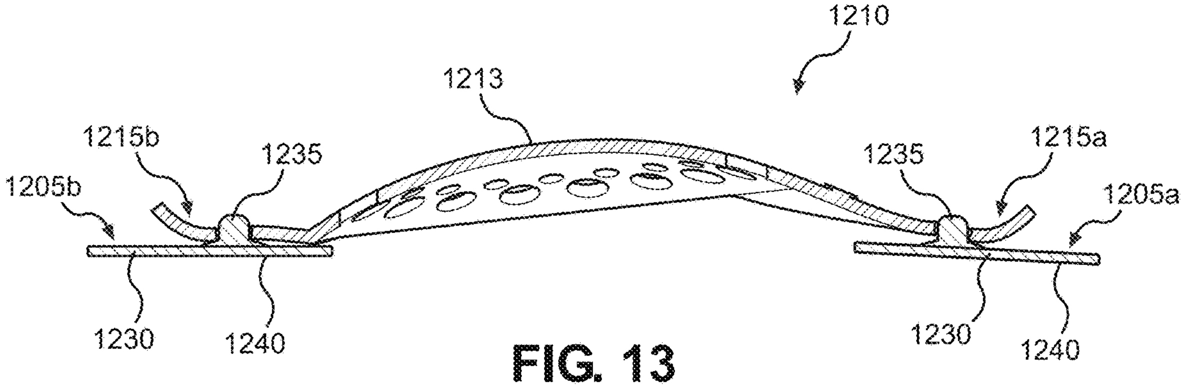

FIGS. 12 and 13 show an example of an eye shield assembly 1210 in accordance with aspects of the invention. FIG. 12 shows an isometric view of the eye shield assembly 1210, while FIG. 13 shows a cutaway side view of the eye shield assembly 1210. As shown in FIGS. 12 and 13, the eye shield assembly 1210 includes eye shield 1200 and anchors **1205*a*, 1205*b*. In embodiments, the eye shield 1200 includes a main portion 1213, a first end 1215*a* extending from a first side of the main portion 1213, and a second end 1215*b* extending from a second side of the main portion 1213 opposite the first side. In embodiments, the main portion 1213 is configured to cover a patient's eye when the eye shield assembly 1210 is affixed to the patient's face. The main portion 1213 may have a circular shape as shown or any other suitable shape. The main portion 1213 may have multiple through holes that reduce the weight of the eye shield 1200 and promote airflow around the patient's eye. In embodiments, the first end 1215*a* and the second end 1215*b* are configured to selective attach the eye shield 1200 to the anchors 1205*a*, 1205*b*. In the embodiment shown in FIGS. 12 and 13**, the attachment is made using a snap connection system.

Similar to the eye shield 200, the eye shield 1200 is configured to be affixed over the patient's eye cavity in an orientation that is generally from cheek to the mid-brow line with the bottom of the tear-drop shape pointing in the upward direction. According to aspects of the invention, the eye shield 1200 includes a first end and a second end, the first end being connected to a first anchor **1205*a* affixed to the patient's face at a first location and the second end being affixed to a second anchor 1205*b* affixed to the patient's face at a second location. In accordance with aspects of the invention, the eye shield 1200 is selectively detachable from the anchors 1205*a*, 1205*b* while the anchors 1205*a*, 1205*b* remain affixed to the patient's face. In this manner, the eye shield 1200 may be temporarily detached from one or both anchors 1205*a*, 1205*b*, for example to permit examination of the eye by a doctor, and then reattached to the same anchors, all without removing the anchors 1205*a*, 1205*b*** from the patient's skin.

In embodiments, the eye shield 1200 is made of polycarbonate due to its ease of manufacturability and structural properties. Other suitable materials may also be used to construct the eye shield 1200. The eye shield 1200 may be transparent (e.g., clear), translucent (e.g., tinted), or opaque. The eye shield 1200 may optionally include indicia 217 as described with eye shield 200.

Figure 17:
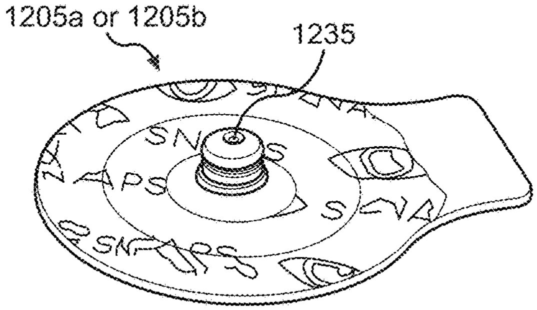
Figure 18:
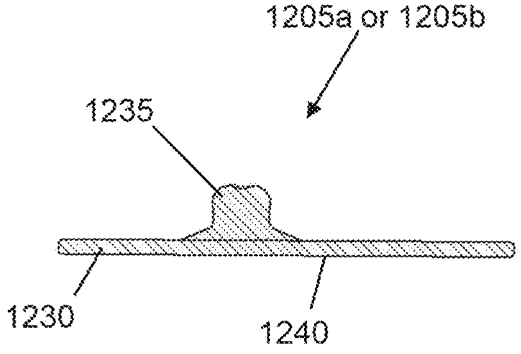

In embodiments, and as shown in FIGS. 13, 17, and 18, each anchor 1205*a*, 1205*b* comprises a substrate 1230, a protrusion 1235 on a top side of the substrate 1230, and an adhesive 1240 on a bottom side of the substrate 1230 opposite the top side of the substrate. The substrate 1230 may be composed of foam or other suitable material. The adhesive 1240 may be an adhesive that is suitable for use with human skin. A peelable backing layer may cover the adhesive 1240 on the bottom side of the substrate 1230 until the anchor is ready to be affixed to patient, at which time the health care provider may peel away the backing layer to expose the adhesive 1240 and then affix the anchor to the patient's skin utilizing the now exposed adhesive 1240. In embodiments, the protrusion 1235 is a shape that extends upward from on the top side of the substrate 1230. In embodiments, the protrusion 1235 is formed using a metallic element that is permanently affixed to the top side of the substrate 1230, although other suitable materials may be used. In embodiments, the protrusion 1235 has the shape of a male half of snap fastener, although other suitable shapes may be used. In one example, each anchor 1205*a*, 1205*b* comprises a commercially available ECG/EKG electrode, with the metallic contact of the electrode comprising the protrusion 1235.

Figure 14:
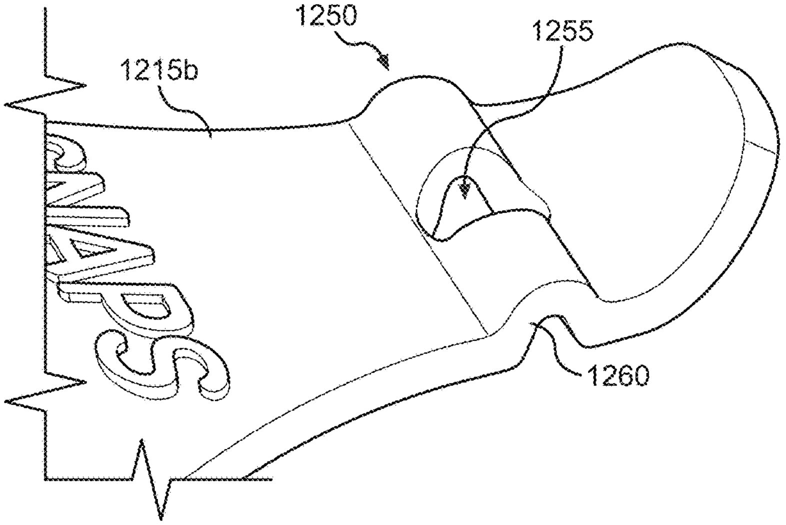
Figure 15:
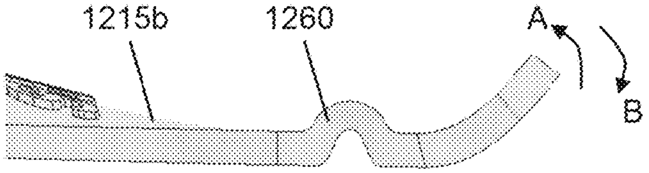
Figure 16:
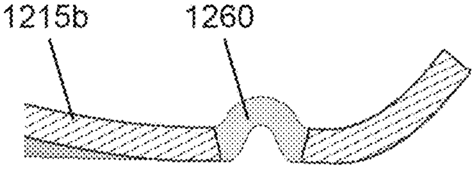

In accordance with aspects of the invention, and as shown in FIG. 12, each of the first end 1215*a* and the second end 1215*b* of the eye shield 1200 comprises a structure 1250 that functions as a female half of a snap fastener that is configured to selectively engage and disengage the protrusion 1235 of one of the anchors 1205*a*, 1205*b*. FIGS. 14, 15, and 16 show an example of the structure 1250 at the second end 1215*b*.

In embodiments, the structure 1250 comprises a cavity 1255 that is sized and shaped to receive and retain the protrusion 1235 in the manner of a snap fastener. In the example shown in FIG. 14, the cavity 1255 comprises a hole through the material of the eye shield 1200, although the cavity 1255 need not be a through-hole. In the example shown in FIGS. 14-16, the cavity 1255 is located at a bend 1260 in the material of the material of the eye shield 1200. In accordance with aspects of the invention, the bend 1260 provides a hinge release mechanism for the eye shield 1200 relative to the protrusion 1235. In embodiments, the structure 1250 is constructed of a material that permits flexure of the material when a force is applied, and the material resiliently returns to its original shape when the force is removed. For example, with reference to FIG. 15, a user may apply a force in the direction of arrow A and this force will cause the second end 1215*b* to bend upward in the direction of arrow A. In this same example, when the user removes the force, the second end 1215*b* will return to its original shape by moving in the direction of arrow B.

In accordance with aspects of the invention, a user may attach the eye shield 1200 to one of the anchors 1205*a*, 1205*b* by pressing one of the ends of the eye shield onto the anchor, such that the cavity 1255 snaps onto the protrusion 1235.

According to aspects of the invention, when a user bends the second end 1215*b* in the direction shown by arrow A in FIG. 15, this bending changes the shape of the cavity 1255 such that the cavity 1255 more easily releases the protrusion 1235 compared to the original shape of the cavity 1255 when the end is not bent. In this manner, the user may bend the end (e.g., the second end 1215*b*) upward to easily disengage the eye shield 1200 from the anchor 1205*b*. Although other types of snap fitting may be used, the inventors have found that the mechanism shown in FIGS. 14-16, which flexes to change the shape of the cavity 1255, reduces the likelihood that the user inadvertently pulls the anchor 1205*b* off the patient's skin when the user is attempting to disengage the eye shield 1200 from the anchor 1205*b*. The function described with respect to the second end 1215*b* in FIGS. 14-16 applies equally to the first end 1215*a*, which has a similar structure 1250 comprising a cavity 1255 that is sized and shaped to receive and retain the protrusion 1235 of the anchor 1205*a*. The user may also utilize this bending when attaching an end of the eye shield to one of the anchors, to change the shape of the cavity such that less pushing force is required to snap the cavity onto the protrusion. Doing so can advantageously decrease discomfort of the patient when reattaching the eye shield to an anchor that is already affixed to the patient's skin.

Additional aspects of the invention include manufacturing and/or using an eye shield (200 or 200" or 200'" or 200"" or 1200) or an eye shield assembly as described herein. Even further aspects of the invention include providing instructions for using an eye shield (200 or 200" or 200'" or 200"" or 1200) or an eye shield assembly as described herein. The instructions may be at least one of printed and video.

Although embodiments have been described thus far with respect to eye shields and eye shield assemblies, implementations of the invention are not limited to use with eye shields and instead can be used with other devices that are attached to the skin of a person. As but one example, implementations may be used to selectively attach and detach a bandage, dressing, or other wearable device using semi-permanent anchors in a manner similar to that described herein.

It is noted that the foregoing examples have been provided merely for the purpose of explanation and are in no way to be construed as limiting of implementations of the present invention. While aspects of the present invention have been described with reference to an exemplary embodiment, it is understood that the words which have been used herein are words of description and illustration, rather than words of limitation. Changes may be made, within the purview of the appended claims, as presently stated and as amended, without departing from the scope and spirit of the present disclosure in its aspects. Although implementations of the present invention have been described herein with reference to particular means, materials and embodiments, implementations of the present invention are not intended to be limited to the particulars disclosed herein; rather, implementations of the present invention extend to all functionally equivalent structures, methods and uses, such as are within the scope of the appended claims.

What is claimed:

1. A wearable medical device assembly for therapeutic treatment of a person, comprising:

- a wearable medical device configured to be applied over a portion of the person;
- a first anchor and a second anchor each comprising an adhesive configured to affix the respective anchor to skin of the person; and
- an attachment system that selectively attaches the wearable medical device to the first anchor and the second anchor, wherein the attachment system permits the wearable medical device to be detached from, and re-attached to, one or both of the anchors while both of the anchors remain affixed to the skin;
- wherein the wearable medical device comprises: an eye shield that is configured to cover an eye of the person; a first end extending radially outward from a first side of the eye shield; and a second end extending radially outward from a second side of the eye shield opposite the first side of the eye shield;

wherein the attachment system comprises: a first snap attachment system between the first end of the wearable medical device and the first anchor; and a second snap attachment system between the second end of the wearable medical device and the second anchor, wherein the first anchor includes a first protrusion that comprises a male half of the first snap attachment system;

wherein the first end of the wearable medical device includes a first cavity that comprises a female half of the first snap attachment system;

wherein the second anchor includes a second protrusion that comprises a male half of the second snap attachment system;

wherein the second end of the wearable medical device includes a second cavity that comprises a female half of the second snap attachment system;

wherein the first anchor and the second anchor comprise respective electrodes, each of the respective electrodes comprising a substrate, the adhesive on a bottom side of the substrate, and a metallic contact on a top side of the substrate opposite the bottom side of the substrate; and wherein the metallic contact of the respective electrode of the first anchor comprises the first protrusion; and wherein the metallic contact of the respective electrode of the second anchor comprises the second protrusion.

* * * * *